(12) United States Patent
Sun et al.

(10) Patent No.: US 7,983,846 B2
(45) Date of Patent: Jul. 19, 2011

(54) SYSTEMS AND METHODS FOR DETERMINING IN-SITU GAS HYDRATE SATURATION

(75) Inventors: Yue-feng Sun, Harrington Park, NJ (US); David Goldberg, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 690 days.

(21) Appl. No.: 11/662,691

(22) PCT Filed: Sep. 14, 2005

(86) PCT No.: PCT/US2005/032712
§ 371 (c)(1),
(2), (4) Date: Feb. 21, 2008

(87) PCT Pub. No.: WO2006/031872
PCT Pub. Date: Mar. 23, 2006

(65) Prior Publication Data
US 2008/0195320 A1    Aug. 14, 2008

Related U.S. Application Data

(60) Provisional application No. 60/609,911, filed on Sep. 14, 2004.

(51) Int. Cl.
*G01V 9/00* (2006.01)
(52) U.S. Cl. .................................................. 702/11

(58) Field of Classification Search ............... 702/11
See application file for complete search history.

(56) References Cited

U.S. PATENT DOCUMENTS

| 4,704,581 | A | 11/1987 | Clark |
| 4,774,471 | A | 9/1988 | Sims et al. |
| 2004/0032257 | A1 | 2/2004 | Freedman |
| 2005/0279532 | A1* | 12/2005 | Ballantyne et al. ............ 175/40 |

FOREIGN PATENT DOCUMENTS

WO    WO 2006/031872    *    3/2006

OTHER PUBLICATIONS

Ideo, "Compensated Dual Resistivity (CDR)", p. 1, printed Sep. 2010.*
Sun, Y.F. et al., "Dielectric method of high-resolution gas hydrate estimation," Geophys. Res. Lett.; Geophysical Research Letters, Feb. 28, 2005, vol. 32, No. 4, pp. 1-4.

(Continued)

*Primary Examiner* — Michael P Nghiem
(74) *Attorney, Agent, or Firm* — Wilmer Cutler Pickering Hale and Dorr LLP

(57) ABSTRACT

Systems and methods for determining in-situ hydrate saturation of hydrate-bearing formations using dielectric properties of gas hydrate amounts are described. In accordance with one aspect, a method for determining gas-hydrate saturation concentration of hydrate-bearing formations includes collecting data using a dielectric propagation tool indicative of propagation time ($t_{pl}$) and attenuation time ($\alpha$), collecting data indicative of density using a density device, and processing the combination of data indicative of $t_{pl}$, $\alpha$ and density to determine the concentration of gas-hydrate saturation and porosity of the formations.

12 Claims, 6 Drawing Sheets

OTHER PUBLICATIONS

Lee, M. W. et al., "Controls on the Physical Properties of Gas-Hydrate-Bearing Sediments Because of the Interaction Between Gas Hydrate and Porous Media," U.S. Geological Survey Scientific Investigations Report 2005-5143, Aug. 2005, pp. 1-15.

Boissonnas, R. et al., "Electromagnetic modeling and in situ measurement of gas hydrate in natural marine environments," Annals of the New York Academy of Sciences 2000, United States, vol. 912, 2000, pp. 159-166.

Kleinberg, R. L. et al., "Measurements for Assessment of Hydrate Related Geohazards," DOE Award No. DE-FC26-01NT41330—Internet Article, Sep. 2004, Houston, Retrieved from the Internet: URL: http://www.netl.doe.gov/scngo/NaturalGas/hydrates/pdf/Project_pdfs/Measurements%20for20 Assessmentof%20Hydrate%20Related%20Geohazards.pdf>
'retrieved on Dec. 6, 2005, p. 9, last paragraph, penultimate sentence.

Wright, J.F. et al., A Method for Direct Measurement of Gas Hydrate Amounts Based on Bulk Dielectric Properties of Laboratory Test Media,: Proceedings of the Fourth International Conference on Gas Hydrates, May 19, 2002, pp. 745-749.

Collett, T.S. et al., "Detection of Gas Hydrate with Downhole Logs and Assessment of Gas Hydrate Concentrations (Saturations) and Gas Volumes on the Blake Ridge with Electrical Resistivity Log Data," Proceedings of the Ocean Drilling Program, Scientific Results, vol. 164, 2000, pp. 179-191.

Bonner, S. et al., "Resistivity While Drilling—Images from the String," Oilfield Review, vol. 8, No. 1, 1996, pp. 4-19.

International Search Report for International Patent Application No. PCT/US2005/032712.

* cited by examiner

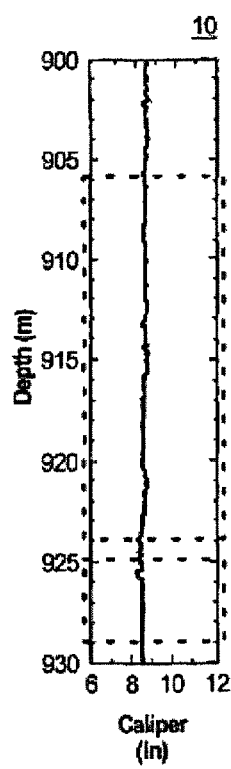
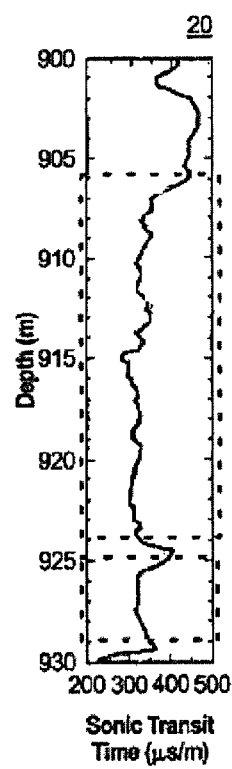
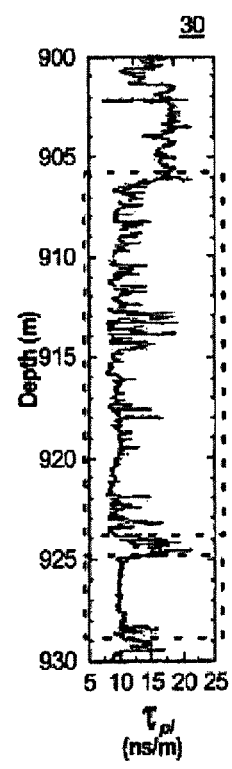
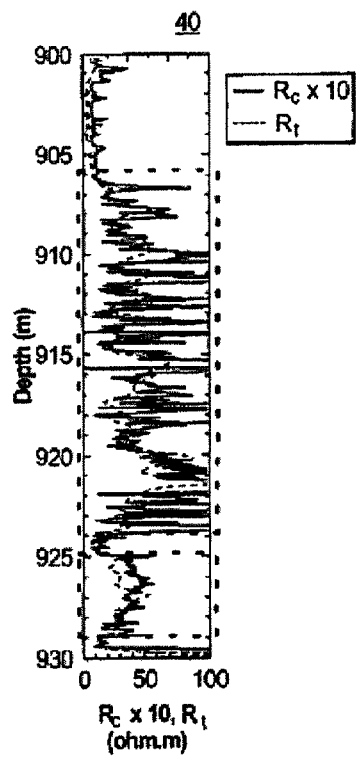
FIG. 1A  FIG. 1B  FIG. 1C  FIG. 1D

SYSTEMS AND METHODS FOR DETERMINING IN-SITU GAS HYDRATE SATURATION

CROSS-REFERENCE TO RELATED APPLICATIONS

This application is a U.S. National Phase Application under 35 U.S.C. §3.71 of International Patent Application No. PCT/US2005/032712, filed Sep. 14, 2005, which claims the benefit of U.S. Provisional Patent Application Ser. No. 60/609,911 filed Sep. 14, 2004, which are both incorporated herewith by reference in their entireties.

BACKGROUND

Gas hydrate is a solid ice-like substance composed of water and gas in which gas molecules are encaged in the rigid lattice of water molecules. Methane hydrate ($CH_4 6H_2O$) consists of about 85% water on a molecular basis. In nature, gas-hydrate-bearing formations are generally multiphase systems consisting of a formation grain matrix with water, gas and hydrate occupying the pore space. Methane hydrate occurs commonly in marine and permafrost sedimentary environments with relatively low temperatures and high formation pressures. Because of its efficient molecular-scale packing, a unit volume of methane hydrate can store more than 160 volumes of free gas equivalent at standard temperature pressure (STP). In addition to representing a potentially vast energy resource for the future, the possible release of large amount of methane gas from geological reservoirs may be an important factor affecting global climate change and local terrain/slope stability.

Although its large natural occurrence has been qualitatively investigated, methods of accurate quantitative assessment of in-situ gas hydrate amounts still need to be improved. Accurate estimation of in-situ hydrate saturation is needed at least for thermodynamic modeling of hydrate dynamics to understand its initiation and dissociation in natural environments.

An evaluation of the properties of gas hydrate-bearing formations has been previously reported for results obtained from downhole log data from a gas hydrate research well. One particular well that has been used to collect data is the JAPEX/JNOC/GSC et al. Mallik 5L-38 Well located at (69°27'39.30"N, 134°39'38.90"W) in the Mackenzie Delta, Northwest Territories, Canada. The base of permafrost in the immediate vicinity of the well is estimated to be at a depth of 600 m beneath ground level. Gas hydrate observed in Mallik 5L-38 Well occurs around the depth of about 1000 m below the ground surface, within the Oligocene, Miocene, and Pliocene sediments composed mainly of weakly cemented sand/sandstone and silt/siltstone. The average formation temperature in the hydrate zones is about 10° C., ranging from 6 to 14° C.

Methods have also previously been developed to estimate hydrate saturation from wireline induction resistivity logs. Logging-while-drilling (LWD) electromagnetic log results in hydrate-bearing formation in the Costa Rica continental margin have been previously reported. Dielectric estimates are a good proxy of in-situ hydrate saturation in, as a minimum, modeling hydrate dynamics. In the prior art, factors including the relatively low frequency (2 MHz) of the measurements did not allow assessment of the dielectric properties of in-situ gas hydrate formation. Dielectric measurements to quantify gas hydrate amounts in laboratory test media have been conducted, however, in-situ dielectric properties of natural gas hydrate have not been previously measured and reported.

Thus, there still remains a need to estimate in-situ hydrate saturation, in particular, determine in-situ dielectric properties of gas hydrate amounts.

SUMMARY OF THE INVENTION

Systems and methods for determining in-situ hydrate saturation of hydrate-bearing formations using dielectric properties of gas hydrate amounts are described. In accordance with one aspect, a method for determining gas-hydrate saturation of hydrate-bearing formations includes collecting data using an electromagnetic propagation tool indicative of propagation time ($t_{pl}$) and attenuation time ($\alpha$), collecting data indicative of density using a density device, and processing the combination of data indicative of $t_{pl}$, $\alpha$ and density to determine the gas-hydrate saturation and porosity of the formations. The method for determining the concentration of gas-hydrate saturation further includes verifying the reliability of a plurality of attenuation time ($\alpha$) measurements.

The dielectric propagation tool includes an antenna array, at least two transmitters aligned with at least two receivers. The dielectric propagation tool operates at a plurality of different frequencies. In one embodiment, the frequency of operation is 1.1 GHz.

In accordance with another aspect, a method for determining in-situ hydrate saturation of hydrate-bearing formations includes collecting data using a dielectric propagation tool indicative of propagation time $t_{pl}$, collecting data using a neutron porosity tool, and processing the combination of data indicative of $t_{pl}$ and neutron porosity to determine the gas-hydrate saturation. Alternate embodiments use other porosity measurements, for example, sonic-derived porosity or resistivity-derived porosity.

In accordance with another aspect, a method for determining in-situ gas-hydrate saturation of a hydrate-bearing formation includes transmitting an electromagnetic wave through at least one portion of the hydrate-bearing formation, determining a propagation time of the electromagnetic wave through each of the at least one portion, determining at least one of the density of each of the at least one portion or the porosity of the hydrate-bearing formation, and computing the gas-hydrate saturation of the hydrate-bearing formation. The method further includes determining an attenuation time of the electromagnetic wave through each of the at least one portion. The propagation time and the attenuation time are collected using a dielectric propagation tool. Based on the computed in-situ gas-hydrate saturation, the method includes determining the energy potential of the hydrate-bearing formation. The computation includes processing data indicative of at least one of the propagation time, attenuation time or density. In the alternative, the computation includes processing data indicative of at least one of the propagation time, attenuation time or porosity. In an alternative, the computation of the gas-hydrate saturation amount includes processing data indicative of the propagation time and density. In another alternative, computing the gas-hydrate saturation includes processing data indicative of the propagation time and porosity.

In accordance with another aspect, a system to determine gas-hydrate saturation of hydrate-bearing formations, includes an electromagnetic propagation tool having at least one transmitter and at least one receiver, a density tool, and a processor that processes data collected to determine at least the gas-hydrate saturation of the formation. The system further includes a porosity tool. The porosity tool is at least one of a neutron-porosity tool, a sonic-derived porosity tool, or a resistivity-derived porosity tool. The system further includes a display in communication with the processor.

The foregoing and other features and advantages of the invention will be apparent from the following more particular description of embodiments of the invention as illustrated in the accompanying drawings.

BRIEF DESCRIPTION OF THE DRAWINGS

FIGS. 1A-1D are graphical representations of a composite log for the depth interval from 900 m to 930 m covering a gas hydrate zone (shaded), wherein FIG. 1A illustrates HCAL: Caliper log showing the borehole condition typical in the hydrate zones in the Mallik 5L-38 well; FIG. 1B illustrates DTCO: Sonic transit time of compressional waves recorded by a Dipole Imager; FIG. 1C illustrates $t_{pl}$: Propagation time recorded by the electromagnetic propagation tool; FIG. 1D illustrates $R_c \times 10$: resistivity derived from the electromagnetic propagation tool with a scale factor of 10 due to frequency dependence; $R_t$ (dotted) and induction resistivity, and wherein hydrate layers are identified as those with a shorter sonic transit time, a shorter propagation time and a higher resistivity.

DETAILED DESCRIPTION

Figure 2:
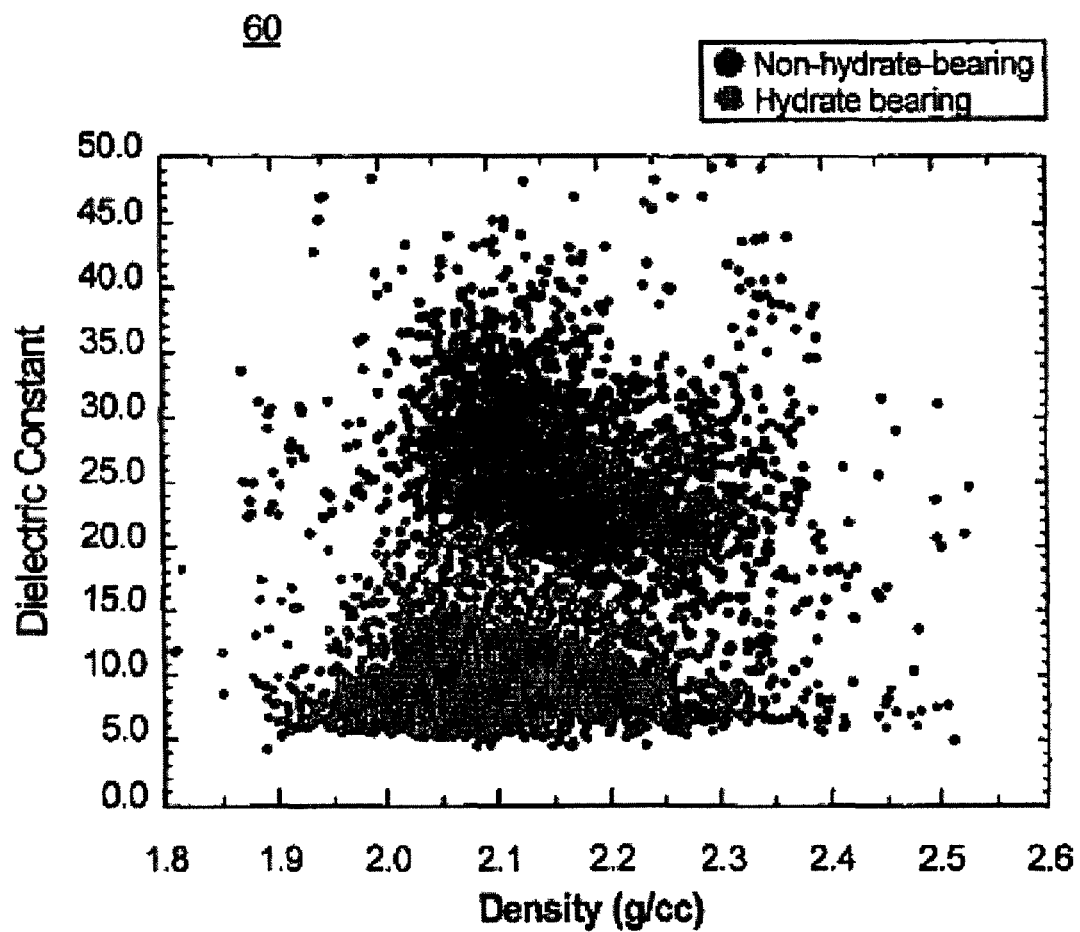
FIG. 2 illustrates a cross-plot of derived dielectric constant versus density log, showing the good separation between gas hydrate (grey) and the non-hydrate formation (black) in accordance with an embodiment.

The embodiments of the present invention include the systems, methods for determining hydrate saturation by analyzing dielectric measurements in gas hydrate reservoirs. A dielectric logging tool, for example, an adaptable electromagnetic propagation tool is used to measure the electromagnetic properties of the hydrate-bearing formations. In-situ bulk dielectric constant and electrical conductivity are calculated from the dielectric measurements. High-resolution estimates of gas-hydrate saturation are obtained from the calculated dielectric property combined with density measurements. In an embodiment, the calculated dielectric property can be combined with neutron porosity measurements. Embodiments include a method that combines in-situ density measurements with the dielectric propagation time measurements to derive in-situ gas-hydrate saturation.

In an embodiment, the dielectric logging device is an antenna pad-type device including two microwave transmitters aligned with two receivers in the middle of the pad, oriented in the direction of and placed along the borehole axis. In an embodiment, the antennas used in the device operate as magnetic dipoles. The antenna array used in the, for example, Mallik Well, called "endfire array", consists of four magnetic dipole antennas oriented in the direction of and placed along the borehole axis. The transmitter-to-receiver spacings are, for example, approximately 8-cm and 12-cm. The unit operates at a frequency of 1.1 GHz and measures both propagation time $t_{pl}$ and attenuation ($\alpha$) of the sinusoidal electromagnetic wave traveling from each transmitter to the two receivers, with a depth sampling rate of about 1.27 cm.

The antenna array is used to increase the depth of investigation (up to, for example, approximately 2.54 to 15.24 cm) and maintain a high vertical resolution (<5 cm). The array device also provides a good measurement in rugose boreholes and significantly reduces mudcake and standoff effects without sacrificing vertical resolution.

In operation, the device is pushed onto the borehole wall. This device configuration enables accurate calculation of the tool response, and the "spread-loss" for attenuation is constant, instead of depending on the propagation time. The measured attenuation $\alpha$ and propagation time $t_{pl}$ are converted to their plane-wave equivalence ($\alpha$ and $t_{pl}$, respectively) before their use for further analysis and interpretation. The plane-wave correction for propagation time due to dipole term is minor, whereas the spread-loss correction for attenuation is significant.

Electromagnetic fields impinged into a macroscopic matter are perturbed by the bounded charges (dielectric property) and the free charges (conductive property). The electromagnetic measurements performed by recording the travel time (or propagation time, $t_{pl}$) and amplitude decay (or attenuation, $\alpha$ can be used to assess both these properties in terms of the relative dielectric constant ($\in_r$) and the conductivity ($\sigma$) of the matter. Both dielectric constant ($\in^r$) and conductivity ($\sigma$) can be calculated from the spread-loss-corrected attenuation ($\alpha$) and dipole-corrected $t_{pl}$ data using the following formula for a sinusoidal tool frequency, for example, the 1.1 GHz dielectric device, which are obtained from the plane-wave solutions of the Maxwell equations:

$$\varepsilon_r = c^2 \left( t_{pl}^2 - \frac{\alpha^2}{2978.5 f^2} \right), \quad (1)$$

$$\sigma = \frac{\alpha t_{pl}}{5458},$$

where $t_{pl}$ is the propagation time in ns/m, $\alpha$ is attenuation in dB/m, $\in_r$ is the relative electric permittivity or dielectric constant (dimensionless), $\sigma$ is the conductivity in Siemens/m or mho/m, and c (=0.3 m/ns) is the speed of light in vacuum and f is the tool frequency which is, for example, 1.1 GHz.

An embodiment of the present invention includes the determination of a petrophysical model. The fundamental law governing electromagnetic wave propagation in both vacuum and matter is best described by Maxwell's equations. When the media can be treated as homogeneous and isotropic at macroscopic scale, the electromagnetic properties can be quantitatively characterized by the dielectric constant, magnetic permeability, and conductivity, which are dependent on frequency, temperature, and pressure. In most dielectric and nonmagnetic materials, magnetic permeability can be assumed to be 1. Embodiments of the present invention adopt an effective-medium approach and assume that the multi-phase system of hydrate-bearing formation can be approximated as a continuous, homogeneous, and isotropic medium. It is assumed that the effective or bulk magnetic permeability of the hydrate-bearing media is 1 and the bulk relative electric permittivity (or the dielectric constant) and the bulk density obey the following laws of mixture via volumetric averaging:

$$\rho = \sum_a \phi_a \rho_a \qquad (2)$$

$$\sqrt{\varepsilon_r} = \sum_a \phi_a \sqrt{\varepsilon_{ra}},$$

$$\sum_a \phi_a = 1,$$

where $\phi_a$, is the volume fraction of the a-th component, i.e., the ratio of the volume of the a-th component to the bulk volume, $\rho_a$ and $\varepsilon_{ra}$ are the density and dielectric constant of the a-th component, respectively. $\rho$ and $\varepsilon_r$ are the bulk density and bulk dielectric constant, respectively. It is assumed that the porous media consists of only three components, namely, solid grain, hydrate, and water. Equation (2) can then be simplified to $$\rho = (1-\phi)\rho_s + \phi S_h \rho_h + \phi(1-S_h)\rho_w,$$

$$\sqrt{\varepsilon_r} = (1-\phi)\sqrt{\varepsilon_{rs}} + \phi S_h \sqrt{\varepsilon_{rh}} + \phi(1-S_h)\sqrt{\varepsilon_{rw}}, \qquad (3)$$

where $\phi$ is the porosity of the total pore space, $S_h$ is the hydrate saturation or the hydrate volume fraction, $\rho_s$, $\rho_h$, and $\rho_w$ are the density of solid grain, gas hydrate, and water, respectively, $\varepsilon_{rs}$ $\varepsilon_{rh}$, and $\varepsilon_{rw}$ are the dielectric constant of solid grain, gas hydrate, and water, respectively.

A preferred embodiment uses $\rho_w$=1.0 g/cc, $\rho_h$=0.92 g/cc, and $\rho_s$=2.65 g/cc. For the 1.1 GHz dielectric device deployed, $\varepsilon_{rw}$=81, $\varepsilon_{rh}$=3, and $\varepsilon_{rs}$=5 which is about the average of the dielectric constants of quartz and illite minerals. The intrinsic dielectric properties of the individual components strongly depend upon temperature, pressure, wave frequency, and the internal structures of the molecules and crystals. The dielectric constant of water used is, $\varepsilon_{rw}$=80, is approximated according to the estimated temperature and pressure ranges and water salinity in the hydrate zones in the Mallik 5L-38 well. The dielectric constant of gas hydrate at 1.1 GHz, is assumed to be similar to ice, $\varepsilon_{rh}$=3, based on laboratory results. Given these intrinsic density and dielectric parameters of individual components, Equation 3 can be solved to calculate simultaneously both the hydrate saturation and porosity of the hydrate-bearing formation from the dielectric and density logs. In the GHz frequency range, the total propagation time is mainly controlled by the dielectric properties of the matter and less affected by attenuation. In the gas hydrate zone studied in Mallik 5L-38, the average correction on propagation time caused by attenuation ranges only from 0 to 10%.

The relative dielectric constant and the conductivity of the matter can be calculated from these two measurements, $t_{pl}$ and $\alpha$ using Equation 1. Equation 1 is valid for homogeneous and isotropic continuous macroscopic matter, without explicitly considering the mesoscopic and/or microscopic structures. Physically it means that the total propagation time $t_{pl}$ is the sum of two parts: the propagation time delay due to the presence of the lossless dielectric matter, and the additional propagation time delay caused by the conducting nature of the materials. The first part of Equation 1 indicates that the relative dielectric constant is simply the square of the lossless formation propagation time multiplied by the square of the speed of light in vacuum. Therefore, the second part of Equation 3 of dielectric constant is a time-averaging equation or the extended $t_{po}$ method of loss-less formation propagation time of gas hydrate formation. In the gas hydrate zone studied in Mallik 5L-38, the average correction on propagation time caused by attenuation ranges from 0 to 10%, dependent on hydrate saturation. It means that the total propagation time is mainly controlled by the dielectric property of the matter and is less affected by attenuation, whereas the attenuation is directly related to the conductivity of the formation.

It is noted that the effective medium model or time-averaging equation of relative dielectric constant used in the method of an embodiment of the present invention is different from other equivalent medium models. In this embodiment no assumption is made about the petrophysical model of conductivity or attenuation. The propagation time is dominated by the dielectric property in gas hydrate at 1.1 GHz. Also, propagation time measurements are usually more accurate than attenuation measurements. Hence, the volumetric averaging law of density is used in combination with the effective medium dielectric model in Equation 3.

With respect to data analysis, the Mallik 5L-38 well was drilled to a total depth of 1165 m and cased at 676.5 m. The dielectric log was recorded from 676.5 m at the bottom of the casing to 1146 m near the bottom of the well. In an embodiment, the depth used for the analysis is the measured log depth, which is the subsurface depth plus the height (4.6 m) above ground surface of the Kelly bushing on the drilling rig. The ground elevation of the well is 1 m above sea level. A nearly complete suite of logging devices, for example, density, neutron-porosity, dipole-sonic, and resistivity tools were deployed in the well.

Electromagnetic propagation time measured from 680 m to 1140 m show similar trends with depth as the sonic transit time, but reveal much higher resolution variations than the sonic log. A composite log including, without limitation, caliper, sonic transit time, electromagnetic propagation time, electromagnetic resistivity, and induction resistivity is shown in FIGS. 1A-1D for the depth interval from 900-930 m (30 m—thick hydrate bearing zone) covering one of the hydrate zones. The caliper log indicates excellent borehole conditions in the hydrate zones, which is essential for the high-frequency and high-resolution dielectric tool. In the intervals containing gas hydrate, electromagnetic waves propagate like sonic waves, faster in hydrate than in non-hydrate zones. As shown in this interval, electromagnetic propagation time $t_{pl}$ shows similar trends with depth as the sonic transit time, but reveals much higher resolution than the sonic log.

The average electromagnetic propagation time is 9.5 ns/m in the hydrate zones, including 905-930 m, 940-990 m, and 1070-1105 m. The average $t_{pl}$ is 18 ns/m in the overlying and underlying clayey sediments. Attenuation measurements ($\alpha$) average 9.7 dB/m in the hydrate zones and 18.5 dB/m elsewhere. The electromagnetic resistivity ($R_c$) derived from the data is generally much lower than the resistivity ($R_t$) derived from an induction tool, typically by a factor of 10. In Mallik 5L-38 Well, $R_c$ needs to be multiplied by a factor of 10 in order to be compared with $R_t$. This may be due to frequency offset differences between the tools which differ substantially and also to their different penetration depths and particularly different fluid salinities. Induction resistivity tools usually operate at about 20 kHz and dielectric tool operates at about 1.1 GHz. The attenuation/conductivity is strongly frequency-dependent. With a factor of 10, $R_c$ agrees quite well with induction resistivity $R_t$ in hydrate zones, but shows much higher vertical resolution, as indicated in FIGS. 1A-1D. The average resistivity from the dielectric device in hydrate zones is >5 ohm.m, ranging from approximately 2-10 ohm.m when measured at 1.1 GHz from the dielectric tool and shows significantly finer vertical resolution than $R_t$.

The dielectric constant is computed from $t_{pl}$ and $\alpha$ as defined by Equation 1. Both the calculated dielectric constant and density log values are low in the hydrate zones. The cross-plot of dielectric constant versus density in FIG. 2 shows the separation between hydrate-bearing sands and other sediments, where low $\in_r$ and density values indicate the former. The average dielectric constant ($\in_r$) in the hydrate zones is 9, ranging from 5 to 20.

Figure 3A:
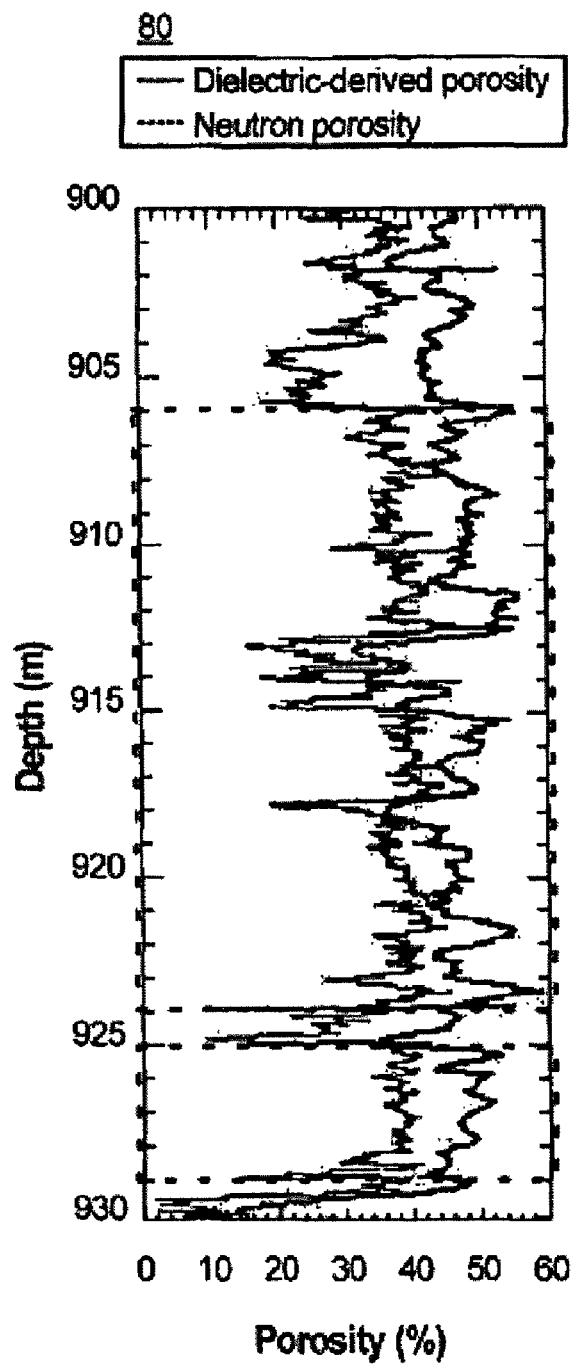
FIGS. 3A and 3B illustrate graphically a portion of estimated hydrate saturation and porosity logs for the hydrate reservoir in the depth interval from 900 m to 930 m in accordance with an embodiment of the present invention, wherein, the dielectric-derived high-resolution estimates (black) is shown against those (dotted) derived from the induction resistivity log ($R_t$), the dielectric-derived porosity (black) is shown against the neutron porosity (dotted), neutron logs overestimate formation porosity. Shaded regions are hydrate-bearing sands.
Figure 3B:
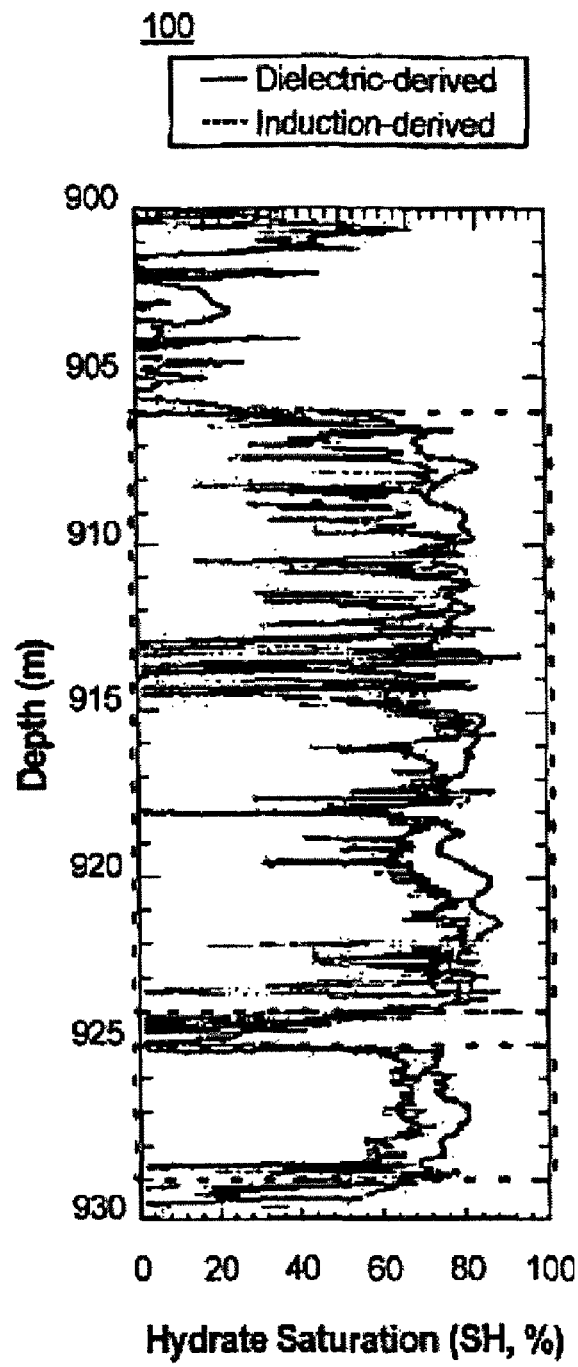

FIGS. 3A and 3B illustrate computed dielectric-derived and induction-derived hydrate saturation for the depth interval from 900 m to 930 m in the Mallik 5L-38 well. Both hydrate saturation and porosity are estimated from the dielectric and density logs using Equation 3. The induction-derived hydrate saturation is calculated from the induction resistivity log ($R_t$). The average hydrate saturation is 70% in hydrate-bearing sands. The dielectric-derived estimates of hydrate saturation have a much higher resolution than those from the induction resistivity log. As illustrated in FIGS. 3A and 3B, the hydrate content from the dielectric device and induction logs often can differ up to 15%. This is because the parameters used in the induction method assume Archie-coefficients approximated only empirically. The dielectric-derived porosity (i.e., the dielectric-density-derived porosity) is also shown in FIGS. 3A and 3B, along with neutron porosity for comparison. Neutron porosity tends to overestimate the true porosity in hydrocarbon-bearing and clay rich formations. The fine structures revealed on both hydrate saturation and porosity data from the dielectric log are thin-bedded clay or silt layers within the sand bodies, consistent with the sedimentological description of the recovered core samples.

The following method is used in accordance with an embodiment to obtain hydrate saturation estimates from induction resistivity log, which uses the Archie equation of electrical resistivity as follows:

$$S_h = 1 - \left(\frac{aR_w}{\phi^m R_t}\right)^{\frac{1}{n}}, \quad (4)$$

where $S_h$ is the hydrate saturation (assuming $S_h=1-S_w$, $S_w$ is the water saturation), $R_t$ is the formation resistivity (from induction log) in ohm.m, $\phi$ is porosity. $R_w$ is the resistivity of formation water, which ranges from about 0.3 to 0.38 ohm.m within the subpermafrost sedimentary section of the Mallik L-38 well. It is assumed that $R_w=0.35$ ohm.m for simplicity. In Equation 4, a, m, and n are three empirical parameters, which are set to 0.62, 2.15, and 1.9386, respectively. The dielectric-density-derived porosity (shown in FIG. 3A) is used in Equation 4, instead of neutron porosity. Neutron porosity overestimates the true porosity because it depends mostly on the hydrogen index of the formation, which is proportional to the quantity of hydrogen in both bound and free water. However, an alternate embodiment uses neutron porosity data. Alternate embodiments use other porosity measurements, for example, sonic-derived porosity data or resistivity-derived porosity data.

Figure 4A:
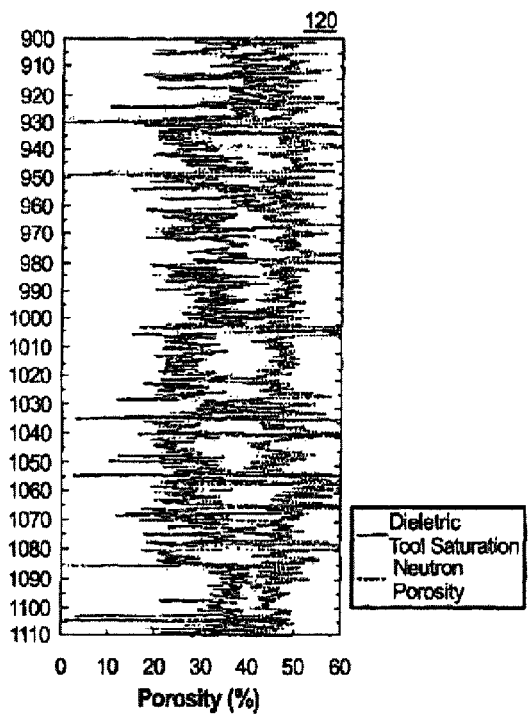
FIGS. 4A and 4B illustrate graphically dielectric-derived hydrate saturation and porosity for the hydrate reservoirs in the Mallik 5L-38 well, showing dielectric saturation estimates in good overall agreement with those from induction resistivity ($R_t$) in accordance with an embodiment of the present invention.
Figure 4B:
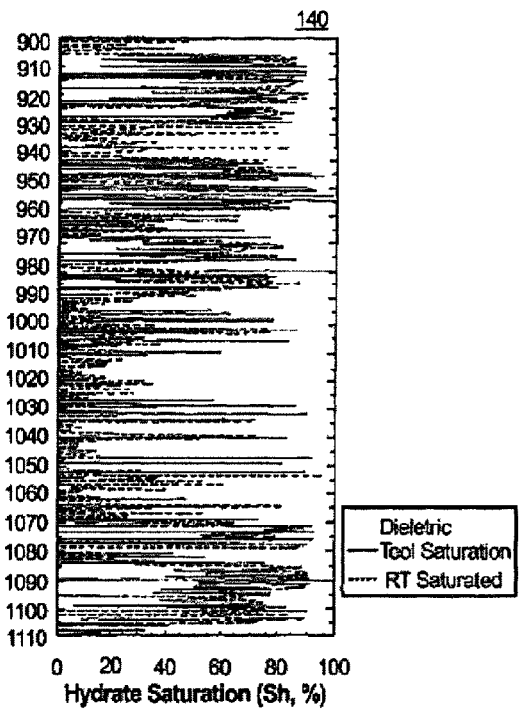

FIGS. 4A and 4B show the dielectric-derived hydrate saturation and porosity for the entire gas hydrate depth interval from 900 m to 1110 m in the Mallik 5L-38 well. The average hydrate saturation is about 80% for the hydrate zones with a variation from 20% to 95%. As shown in FIG. 3B, the dielectric-derived estimates of hydrate saturation have a much higher resolution than those from induction resistivity log. As expected, the dielectric-derived saturation log also has a much higher vertical resolution than the sonic estimates.

Figure 5:
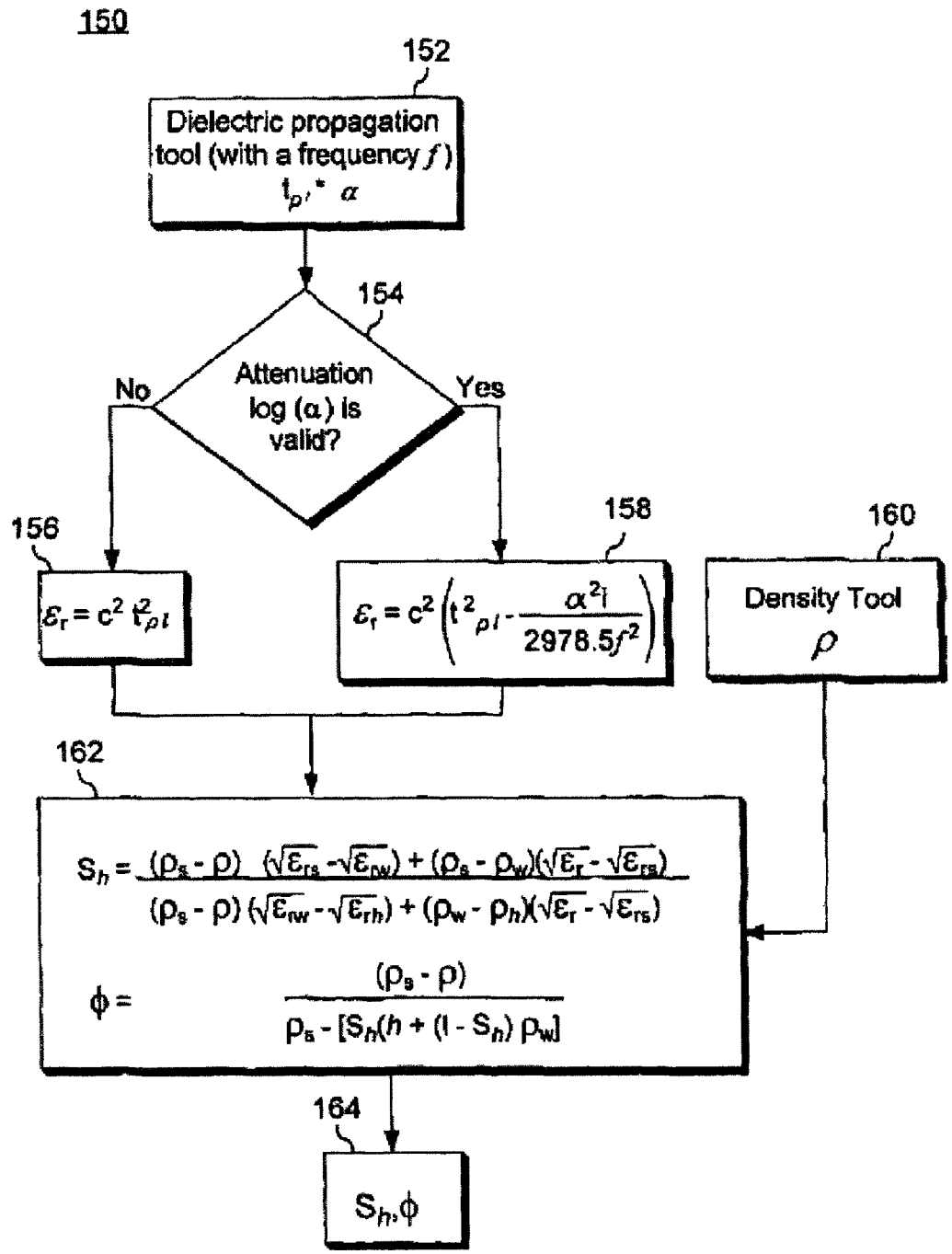
FIG. 5 illustrates a flow chart of a method to determine in-situ gas hydrate amounts in accordance with an embodiment of the present invention.

FIG. 5 is a method 150 to calculate gas-hydrate saturation in accordance with an embodiment of the present invention. The method includes the step 152 for providing the measurements of propagation time (tpl) and attenuation ($\alpha$) using a dielectric propagation tool. Per step 154 it is determined if the attenuation log is valid. If the attenuation log is not valid or reliable then the bulk or average dielectric constant ($\in_r$) is calculated using the equation described in step 156. Using the equation in step 156, $\in_r$ is calculated using propagation time alone. The approximation using propagation time is valid when attenuation values are small. If the attenuation log is reliable then the equation in step 158 is used to calculate $\in_r$. The value $\in_r$ is input into the step 162 along with the data ($\rho$) collected using a density tool per step 160. The equations in step 162 are used to calculate both gas-hydrate saturation and porosity from the dielectric and density measurements. The different component density measures such as the density of sediment (solid grain), hydrate and water as well as the dielectric constant of sediment, hydrate and water are obtained from other measurements or information. The differences between the component values of density and dielectric constants and the ratio, enable the volume fraction of hydrate ($S_h$) to be computed.

The porosity of the composite formation, defined as the water volume in the total sediment/hydrate/water matrix, is determined using the computed $S_h$ and the ratio of density component differences.

The resultant value of $S_h$ is the desired estimated hydrate saturation. The resultant value of porosity ($\phi$) allows for direct comparison with other independent porosity measurements such as, for example, neutron-, sonic-, or resistivity-derived porosity data. The porosity ($\phi$) comparisons provide an indication of the quality of the estimations.

In an embodiment, hydrate saturation is computed using porosity measurements and the measurements of propagation time alone. Equation 3, for example, is used for the calculation of hydrate saturation using the porosity values provided.

In an alternate embodiment, hydrate saturation is computed using porosity measurements and measurements of propagation time and attenuation time. Equation 3, for example, is used for this computation of the hydrate saturation.

Embodiments of the present invention, thus, use wireline dielectric logs to obtain high-resolution estimates of in-situ gas-hydrate saturation. The average hydrate saturation for the entire gas hydrate interval in the Mallik 5L-38 well is about 80% with a variation from 20% to 95%. The relative electric permittivity or dielectric constant in the hydrate zones is 9, ranging from 5 to 20, depending on hydrate saturation. The average resistivity in hydrate zones is >5 ohm.m, ranging from 2-10 ohm.m at 1.1 GHz. The dielectric-derived hydrate saturation is in good overall agreement with the induction resistivity estimate. The propagation time and attenuation logs (or their equivalent, dielectric constant and propagation resistivity) show similar trends with sonic and induction resistivity log, but with much finer vertical resolution (<5 cm).

Laboratory studies of dielectric measurements on the natural hydrate samples retrieved from the Mallik 5L-38 well enable calibration of these log results. Such experimental measurements can be conducted using samples under controlled temperature and pressure conditions, similar to the in-situ downhole conditions which provide laboratory calibration.

The embodiments of the present invention demonstrate the usefulness of dielectric logs for quantifying in-situ gas hydrate amounts in geological formations. The methods developed herein also are applicable to gas hydrate amounts in marine environments, provided that the borehole condition is good enough to facilitate the acquisition of high-quality dielectric data or logs. The dielectric data log (measurements) is unique in revealing the fine structures of the hydrate-bearing formation. The dielectric constant and conductivity also depend on the formation texture and pore structures, in addition to the fluid and matrix compositions. These can be exploited to yield insight into the relations between in-situ gas hydrate stability and the physical/geochemical properties of the host sediments, for example, without limitations, grain size, pore geometry, and pore water salinity.

However, when interpreting hydrate concentrations based on electromagnetic wave propagation data, it is important to consider, for multiphase hydrate-bearing porous media the dependence of dielectric properties on the wave frequency, temperature, pressure, pore fluid properties, pore structures, and sediment textures.

In view of the wide variety of embodiments to which the principles of the present invention can be applied, it should be understood that the illustrated embodiments are exemplary only, and should not be taken as limiting the scope of the present invention. For example, the steps of the flow diagrams, for example, FIG. 5, may be taken in sequences other than those described, and more or fewer elements may be used in the diagrams. While various elements of the embodiments have been described as being implemented in software, other embodiments in hardware or firmware implementations may alternatively be used, and vice-versa.

Figure 6:
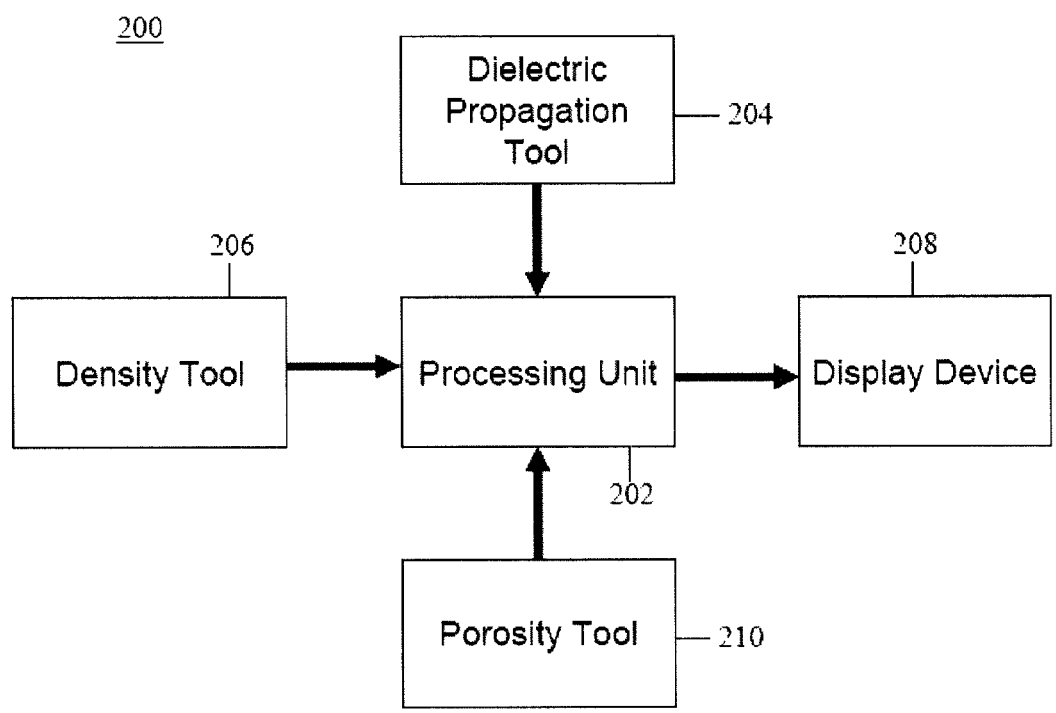
FIG. 6 illustrates a block diagram of a system to determine in-situ gas hydrate amounts in accordance with an embodiment of the present invention.

FIG. 6 is a block diagram showing a system 200 to determine gas-hydrate saturation of hydrate-bearing formations. The system 200 includes an electromagnetic propagation tool 204 having at least one transmitter and at least one receiver, a density tool 206, and a processor 202 that processes data collected at the propagation tool 204 and the density tool 206 to determine at least the gas-hydrate saturation of the formation. The system 200 further includes a porosity tool 210. The porosity tool 210 is at least one of a neutron-porosity tool, a sonic-derived porosity tool, or a resistivity-derived porosity tool. The system 200 further includes a display 208 in communication with the processor 202.

It will be apparent to those of ordinary skill in the art that methods involved in the systems and methods for estimating gas hydrate amounts may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

Other aspects, modifications, and embodiments are within the scope of the following claims.

What is claimed is:

1. A method for determining in-situ gas-hydrate saturation of hydrate-bearing formations, the method comprising:
   collecting data including propagation time (tpl) and an attenuation time ($\alpha$) of an electromagnetic wave transmitted through at least one portion of the hydrate-bearing formations using an electromagnetic propagation tool;
   collecting data including density of the hydrate-bearing formations using a density device; and
   processing, via a processor, a combination of data including at least the propagation time (tpl), the attenuation time, and the density to determine the gas-hydrate saturation and porosity of the hydrate-bearing formations.

2. The method of claim 1, wherein the electromagnetic propagation tool comprises an antenna array and at least two transmitters.

3. The method of claim 2, wherein the at least two transmitters are aligned with at least two receivers.

4. The method of claim 1, wherein the electromagnetic propagation tool operates at a frequency of 1.1 GHz.

5. The method of claim 1, wherein the electromagnetic propagation tool operates in the gigahertz frequency range.

6. The method of claim 1, further comprising verifying a reliability of a plurality of attenuation time (a) measurements from the collecting data.

7. The method of claim 1, wherein the processing comprises calculating a value indicative of average dielectric constant using the propagation time.

8. The method of claim 1, wherein the processing comprises calculating a value indicative of average dielectric constant using the propagation time and the attenuation time.

9. A system to determine gas-hydrate saturation of hydrate-bearing formations, comprising:
   an electromagnetic propagation tool having at least one transmitter and at least one receiver for collecting first data including propagation time (tpl) and attenuation time ($\alpha$) of an electromagnetic wave transmitted from the transmitter through at least one portion of the hydrate-bearing formations;
   a density tool for collecting second data including density of the hydrate-bearing formations; and
   a processor for receiving the first and second data respectively from the electromagnetic propagation tool and the density tool and determining at least the gas-hydrate saturation and estimated porosity of the hydrate-bearing formations using at least the propagation time, the attenuation time, and the density.

10. The system of claim 9, further comprising a porosity tool, wherein the processor receives from the porosity tool third data including porosity of the hydrate-bearing formations for comparing the estimated porosity determined by the processor and the porosity included in the third data to determine a quality of the estimated porosity.

11. The system of claim 10, wherein the porosity tool is at least one of a neutron-porosity tool, a sonic-derived porosity tool, and a resistivity-derived porosity tool.

12. The system of claim 9, further comprising a display in communication with the processor.

* * * * *